(12) United States Patent
Wannberg

(10) Patent No.: US 9,978,579 B2
(45) Date of Patent: *May 22, 2018

(54) ANALYSER ARRANGEMENT FOR PARTICLE SPECTROMETER

(71) Applicant: SCIENTA OMICRON AB, Uppsala (SE)

(72) Inventor: Björn Wannberg, Alfta (SE)

(73) Assignee: SCIENTA OMICRON AB, Uppsala (SE)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/221,340

(22) Filed: Jul. 27, 2016

(65) Prior Publication Data

US 2016/0336166 A1    Nov. 17, 2016

Related U.S. Application Data

(63) Continuation of application No. 14/363,405, filed as application No. PCT/SE2012/050251 on Mar. 6, 2012, now Pat. No. 9,437,408.

(51) Int. Cl.
*H01J 49/48* (2006.01)
*H01J 37/05* (2006.01)
(Continued)

(52) U.S. Cl.
CPC ............. *H01J 49/48* (2013.01); *H01J 37/05* (2013.01); *H01J 49/0031* (2013.01);
(Continued)

(58) Field of Classification Search
USPC ........................................................ 250/307
See application file for complete search history.

(56) References Cited

U.S. PATENT DOCUMENTS

| 1,773,980 A | 8/1930 | Farnsworth |
| 3,749,926 A | 7/1973 | Lee |

(Continued)

FOREIGN PATENT DOCUMENTS

| CN | 101627455 A | 1/2010 |
| DE | 2105805 B2 | 10/1979 |

(Continued)

OTHER PUBLICATIONS

Damascelli et, al., "Angle-resolved Photoemission Studies of the Cuprate Superconductors", Reviews of Modern Physics, vol. 75, Apr. 2003, pp. 473-541.
(Continued)

*Primary Examiner* — Phillip A Johnston
(74) *Attorney, Agent, or Firm* — Morrison & Foerster LLP

(57) ABSTRACT

The present invention relates to a method for determining at least one parameter related to charged particles emitted from a particle emitting sample, e.g. a parameter related to the energies, the start directions, the start positions or the spin of the particles. The method comprises the steps of guiding a beam of charged particles into an entrance of a measurement region by means of a lens system, and detecting positions of the particles indicative of said at least one parameter within the measurement region. Furthermore, the method comprises the steps of deflecting the particle beam at least twice in the same coordinate direction before entrance of the particle beam into the measurement region. Thereby, both the position and the direction of the particle beam at the entrance of the measurement region can be controlled in a way that to some extent eliminates the need for physical manipulation of the sample. This in turn allows the sample to be efficiently cooled such that the energy resolution in energy measurements can be improved.

19 Claims, 8 Drawing Sheets

(51) Int. Cl.
   *H01J 49/00*    (2006.01)
   *H01J 49/06*    (2006.01)
   *G01N 23/227*   (2018.01)

(52) U.S. Cl.
   CPC ............ *H01J 49/06* (2013.01); *H01J 49/061* (2013.01); *G01N 23/2273* (2013.01); *G01N 2223/085* (2013.01); *H01J 49/484* (2013.01); *H01J 2237/0535* (2013.01)

(56) References Cited

U.S. PATENT DOCUMENTS

| | | | | |
|---|---|---|---|---|
| 3,909,610 | A * | 9/1975 | Kokubo | H01J 37/256 250/305 |
| 4,358,680 | A | 11/1982 | Read | |
| 4,427,885 | A | 1/1984 | Takeda et al. | |
| 4,639,602 | A | 1/1987 | Henzler | |
| 4,758,723 | A | 7/1988 | Wardell et al. | |
| 5,097,126 | A * | 3/1992 | Krivanek | H01J 37/261 250/305 |
| 5,185,524 | A | 2/1993 | Page et al. | |
| 5,285,066 | A * | 2/1994 | Sekine | H01J 49/484 250/305 |
| 5,286,974 | A | 2/1994 | Walker et al. | |
| 5,506,414 | A | 4/1996 | Coxon et al. | |
| 5,650,628 | A | 7/1997 | Gordon et al. | |
| 6,064,071 | A | 5/2000 | Nakasuji | |
| 6,104,029 | A * | 8/2000 | Coxon | H01J 49/067 250/305 |
| 6,198,095 | B1 * | 3/2001 | Staib | H01J 37/252 250/287 |
| 6,212,257 | B1 | 4/2001 | Mattern et al. | |
| 6,946,657 | B2 | 9/2005 | Kienzle et al. | |
| 7,411,188 | B2 * | 8/2008 | deCecco | H03F 1/26 250/305 |
| 9,305,745 | B2 * | 4/2016 | Mori | H01J 37/05 |
| 9,437,408 | B2 * | 9/2016 | Wannberg | H01J 37/05 |
| 2002/0140383 | A1 | 10/2002 | Ogasawara | |
| 2006/0060770 | A1 | 3/2006 | Page et al. | |
| 2009/0101819 | A1 | 4/2009 | Zhou et al. | |
| 2013/0126727 | A1 | 5/2013 | Jozwiak et al. | |

FOREIGN PATENT DOCUMENTS

| | | |
|---|---|---|
| EP | 0152502 A1 | 8/1985 |
| GB | 1328713 A | 8/1973 |
| GB | 2064213 A | 6/1981 |
| JP | 47-45369 A | 12/1972 |
| JP | 58-200144 A | 11/1983 |
| JP | 62-6303 B2 | 2/1987 |
| JP | 62-143354 A | 6/1987 |
| JP | 62-167452 A | 7/1987 |
| JP | 01-274050 A | 11/1989 |
| JP | 5-10897 A | 1/1993 |
| JP | 07-270348 A | 10/1995 |
| JP | 2000-164166 A | 6/2000 |
| JP | 2001-266788 A | 9/2001 |
| JP | 2002-299207 A | 10/2002 |
| JP | 2003-207470 A | 7/2003 |
| JP | 2015-45653 A | 3/2015 |
| JP | 2015-511055 A | 4/2015 |
| JP | 2016-197124 A | 11/2016 |
| WO | 2011/019457 A1 | 2/2011 |
| WO | 2013/133739 A1 | 9/2013 |

OTHER PUBLICATIONS

Third Party Observation received for Japanese Patent Application No. 2014-560888, mailed on Dec. 13, 2016, 79 Pages. (48 pages of English Translation and 31 pages of Official Copy).
Advisory Action received for U.S. Appl. No. 14/363,405, dated Sep. 30, 2015, 3 pages.
Baltzer et al., "Optimization and Redesign of an Electron Spectrometer for High-Resolution Gas Phase UV Photoelectron, Auger Electron, and Ion Fragment Spectroscopy", Review of Scientific Instrument, vol. 62, No. 3, Mar. 1991, pp. 643-654.
Baltzer et al., "Optimization and Redesign of an Electron Spectrometer for High-Resolution Gas Phase UV Photoelectron, Auger Electron, and Ion Fragment Spectroscopy", Thesis by Peter Baltzer, UUIP-1182, Uppsala University, Institute of Physics, Sweden, Apr. 1989, pp. 1-30.
Decision to Grant received for European Patent Application No. 14185601.3, dated Sep. 22, 2016, 2 pages.
Email from Anders Lindgren with Brann AB, Intellectual Property Law Firm, dated Apr. 25, 2016, 2 pages.
Extended European Search Report received for European Patent Application No. 12870629.8, dated Sep. 4, 2015, 9 Pages.
Extended European Search Report received for European Patent Application No. 14185601.3, dated Feb. 25, 2015, 7 pages.
Final Office Action received for U.S. Appl. No. 14/363,405 dated Jun. 5, 2015, 16 pages.
Intention to Grant received for European Patent Application No. 14185601.3, dated Jul. 25, 2016, 10 pages.
International Preliminary Report on Patentability received for PCT Patent Application No. PCT/SE2012/050251, dated Sep. 18, 2014, 7 pages.
International Search Report and Written Opinion received for PCT Patent Application No. PCT/SE2012/050251, dated Nov. 26, 2012, 9 Pages.
Jozwiak et al., "A High-Efficiency Spin-Resolved Photoemission Spectrometer Combining Time-of-Flight Spectroscopy with Exchange-Scattering Polarimetry", Review of Scientific Instrument, vol. 81, 053904, 2010, pp. 1-16.
Jozwiak, Chris, "High Efficiency Spin-Resolved ARPES of a Topological Insulator with the Spin-TOF Analyzer", Advanced Light Source User Meeting, Oct. 5, 2011, 23 Pages.
Jozwiak, Chris, "High-Efficiency Spin-Resolved ARPES of a Topological Insulator with the Spin-TOF Analyzer", 2011 Advanced Light Source User Meeting, U.S. Department of Energy, Oct. 5, 2011, 19 pages.
Jozwiak, Christopher M., "A New Spin on Photoemission Spectroscopy", A Dissertation Submitted in Partial Satisfaction of the Requirements for the Degree of Doctor of Philosophy, 2008, 259 pages.
Lee et al., "Photo emission Electron Spectroscopy IV: Angle-Resolved Photoemission Spectroscopy", Journal of Surface Analysis, vol. 17, No. 2, 2010, pp. 64-86.
Martensson et al., "A Very High Resolution Electron Spectrometer", Journal of Electron Spectroscopy and Related Phenomena, vol. 70, 1994, pp. 117-128.
Non-Final Office Action received for U.S. Appl. No. 14/363,405, dated Jan. 23, 2015, 14 pages.
Non-Final Office Action received for U.S. Appl. No. 14/363,405, dated Nov. 13, 2015, 13 pages.
Notice of Allowance received for U.S. Appl. No. 14/363,405, dated Apr. 27, 2016, 9 pages.
Office Action received for Chinese Patent Application No. 201280065644.8, dated Feb. 1, 2016, 21 pages.
Office Action received for European Patent Application No. 14185601.3 dated Dec. 18, 2015, 5 pages.
Office Action received for Japanese Patent Application No. 2014-206185, dated Mar. 2, 2015, 9 pages.
Office Action received for Japanese Patent Application No. 2014-560888, dated Jan. 25, 2016, 8 pages.
Office Action Received for Swedish Patent Application No. 1450816-2, dated Feb. 2, 2015, 4 pages.
Office Action Received for Swedish Patent Application No. 1450816-2, dated Feb. 4, 2015, 1 page.
Office Action Received for Swedish Patent Application No. 1450816-2, dated Feb. 16, 2015, 1 page.
Scienta Instrument, "Scienta Instrument AB 'SES-200'", May 15, 1997, 1 page of Diagram only.
Tanaka et al., "Evolution of the Electronic Structure from the Insulator to the Superconductor in Bi2Sr2-xLax (Ca,Y) Cu2O8δ", Feb. 15, 2010, 13 pages.

(56) References Cited

OTHER PUBLICATIONS

Third Party Observation directed to SE Application No. 1450816-2, Feb. 13, 2015, 2 pages.
Third Party Observation received for European Patent Application No. 14185601.3, mailed on Nov. 20, 2015, 14 pages.
Third Party Observation received for European Patent Application No. 12870629.8, mailed on Aug. 23, 2016, 12 pages.
Third Party Observations filed for the European Patent Application No. 12870629.8 on Mar. 17, 2015, 8 pages.
Third Party Observations received for European Patent Application No. 14185601.3, mailed on Mar. 22, 2016, 40 pages.
Third Party Observations received for European Patent Application No. 14185601.3, mailed on Mar. 29, 2016, 31 pages.
Third Party Observations received for Swedish Application No. 1450816-2, printed on May 9, 2016, 87 pages.
Third Party Observations received for Swedish Application No. 1451107-5, printed on May 9, 2016, 92 pages.
"Operation of the Angle Resolving Lens on Theta Probe", Application Note 31003 Thermo Scientific Inc. 2008, 4 pages.
"Supply of an Ambient Pressure Photoemission End Station for Beamline 24", Technical Description Dossier, Sep. 29, 2008, 43 pages.
Bostwick, Aaron, "Maestro, A New Facility for Arpes at the ALS", Workshop on Novel Trends in Photoemission, Oct. 2011, 19 pages.
Fedorov et al., "Workshop on Novel Trends in Photoemission", Lawrence Berkeley National Laboratory, Oct. 4-5, 2011, 3 pages.
Maehl et al., "A Novel Spectrometer for Near Ambient Pressure Photoelectron Spectroscopy", PHOIBOS 150 NAP Specifications, 2009, 1 page.
Notice of Opposition received for European Patent Application No. 14185601.3, mailed on Nov. 10, 2016, 77 pages (28 pages of English Translation and 49 pages of Official copy).
Office Action received for European Patent Application No. 12870629.8, dated Jul. 1, 2016, 4 pages.
Rotenberg et al., "An Improved Electron Detection System for Extreme Angle-Resolved Photoemission Experiments", Report on Ernest Orlando Lawrence Berkeley National Laboratory, Laboratory Directed Research and Development Program, Mar. 2010, 2 pages.
Rotenberg et al., "An Improved Electron Detection System for Extreme Angle-Resolved Photoemission Experiments", Report on Ernest Orlando Lawrence Berkeley National Laboratory, Laboratory Directed Research and Development Program, May 2011, 2 pages.
"Circuit diagram Hardware Type 102—Wiring X1 (CCD with Deflector)", 1 page.
"Circuit diagram Hardware Type 107—Wiring X7 (Wide angle pre lens with Deflector)", 1 page.
E-mail from Sven Mähl from Apr. 13, 2010, to Andrey Shavorskiy, 2 pages.
"Hardware Type and Backplane Wiring", Specs Surface Nano Analysis GmbH HSA 3500 plus 2.1, Chapter. 8, Jan. 4, 2012, pp. 55-61.
"PHOIBOS 150 NAP; Near Ambient Pressure Hemispherical Energy Analyzer", SPECS, Innovation in Surface Spectroscopy and Microscopy Systems, 2010, 8 pages.
Vos et al., "High-Energy (e, 2e) Spectrometer for the Study of the Spectral Momentum Density of Materials", Review of Scientific Instruments, vol. 71, No. 10, Oct. 2000, pp. 3831-3840.
Vos et al., "Probing the Spectral Densities over the Full Three-Dimensional Momentum Space", Journal of Physics and Chemistry of Solids, vol. 65, 2004, pp. 2035-2039.
Office Action received for Japanese Patent Application No. 2014-560888, dated Oct. 17, 2016, 7 Pages (4 pages of English Translation and 3 pages of Official Copy).
Office Action received for Japanese Patent Application No. 2016-145165, dated Oct. 17, 2016, 8 Pages (4 pages of English Translation and 4 pages of Official Copy).
Third Party Observation received for Japanese Patent Application No. 2014560888, mailed on Aug. 28, 2017, 5 pages (2 pages of English Translation and 3 pages of Official copy).
Notice of Opposition received for European Patent Application No. 14185601.3, mailed on Jun. 30, 2017, 34 pages.
"User Manual for Scienta Electron Spectrometer SES 200", Apr. 15, 1996, 261 pages.
Valla, T., "ARPES at ESM", Presentation, Brookhaven National Laboratory, 31 pages.
Office Action received for European Patent Application No. 12870629.8, dated May 16, 2017, 5 pages.
Office Action received for Japanese Patent Application No. 2014-560888, dated May 29, 2017, 7 pages (4 pages of English Translation and 3 pages of Official Copy).
"The Gammadata Scienta SES-2002 User's Manual" Scienta Instrumnets AB, Mar. 11, 2002, 66 pages.
Notice of Opposition received for Swedish Patent Application No. 1451107-5, mailed on Dec. 1, 2017, 53 pages (21 pages of English translation and 32 pages of Offical Copy).
Request for Invalidation received for Chinese Patent Application No. 201280065644.8, mailed on Nov. 29, 2017, 66 pages (36 pages of English translation and 30 pages of Offical Copy).
Notice of Matters in Trial Examination received for Japanese Patent Application No. 2014-560888, mailed on Jan. 16, 2018, 9 pages (5 pages of English Translation and 4 pages of Offical Copy Only).
Third Party Observation received for Japanese Patent Application No. 2014-560888, mailed on Dec. 19, 2017, 5 pages (3 pages of English Translation and 2 pages of Offical Copy).
Intention to Grant received for European Patent Application No. 12870629.8, dated Mar. 1, 2018, 8 pages.
Office Action received for Korean Patent Application No. 10-2014-7019572, dated Jan. 25, 2018, 11 pages (5 pages of English Translation and 6 pages of Official Copy).
Third Party Opposition Written Summaries received for Japanese Patent Application No. 2017-800082, mailed on Mar. 1, 2018, 15 pages (7 pages of English Translation and 8 pages of Official Copy).
Third Party Opposition Written Summaries received for Japanese Patent Application No. 2017-800082, mailed on Mar. 2, 2018, 17 pages (8 pages of English Translation and 9 pages of Official Copy).
Third Party Observation Written Inquiry received for Japanese Patent Application No. 2017-800082, mailed on Mar. 12, 2018, 4 pages (2 pages of English Translation and 2 pages Official Copy).
Third Party Observation Written Response received for Japanese Patent Application No. 2017-800082, mailed on Mar. 13, 2018, 6 pages (3 pages of English Translation and 3 pages of Official Copy).
Third Party Observation Written Response received for Japanese Patent Application No. 2017-800082, mailed on Mar. 14, 2018, 7 pages (3 pages of English Translation and 4 pages of Official Copy).
Third Party Observation received for Invalidation Trial No. 2017-800082 (for Japanese Patent No. 5815826), mailed on Dec. 19, 2017, 5 pages (3 pages of English Translation and 2 pages of Official Copy).
Notice of Matters received for Invalidation Trial No. 2017-800082 (for Japanese Patent No. 5815826), received on Jan. 16, 2018, 9 pages (5 pages of English Translation and 4 pages of Official Copy).
Third Party Opposition Written Summaries received for Invalidation Trial No. 2017-800082 (for Japanese Patent No. 5815826), mailed on Mar. 1, 2018, 15 pages (7 pages of English Translation and 8 pages of Official Copy).
Third Party Opposition Written Summaries received for Invalidation Trial No. 2017-800082 (for Japanese Patent No. 5815826), mailed on Mar. 2, 2018, 17 pages (8 pages of English Translation and 9 pages of Official Copy).
Third Party Observation Written Inquiry received for Invalidation Trial No. 2017-800082 (for Japanese Patent No. 5815826), mailed on Mar. 12, 2018, 4 pages (2 pages of English Translation and 2 pages Official Copy).
Third Party Observation Written Response received for Invalidation Trial No. 2017-800082 (for Japanese Patent No. 5815826), mailed on Mar. 13, 2018, 6 pages (3 pages of English Translation and 3 pages Of Official Copy).

(56) References Cited

OTHER PUBLICATIONS

Third Party Observation Written Response received for Invalidation Trial No. 2017-800082 (for Japanese Patent No. 5815826), mailed on Mar. 14, 2018, 7 pages (3 pages of English Translation and 4 pages of Official Copy).

* cited by examiner

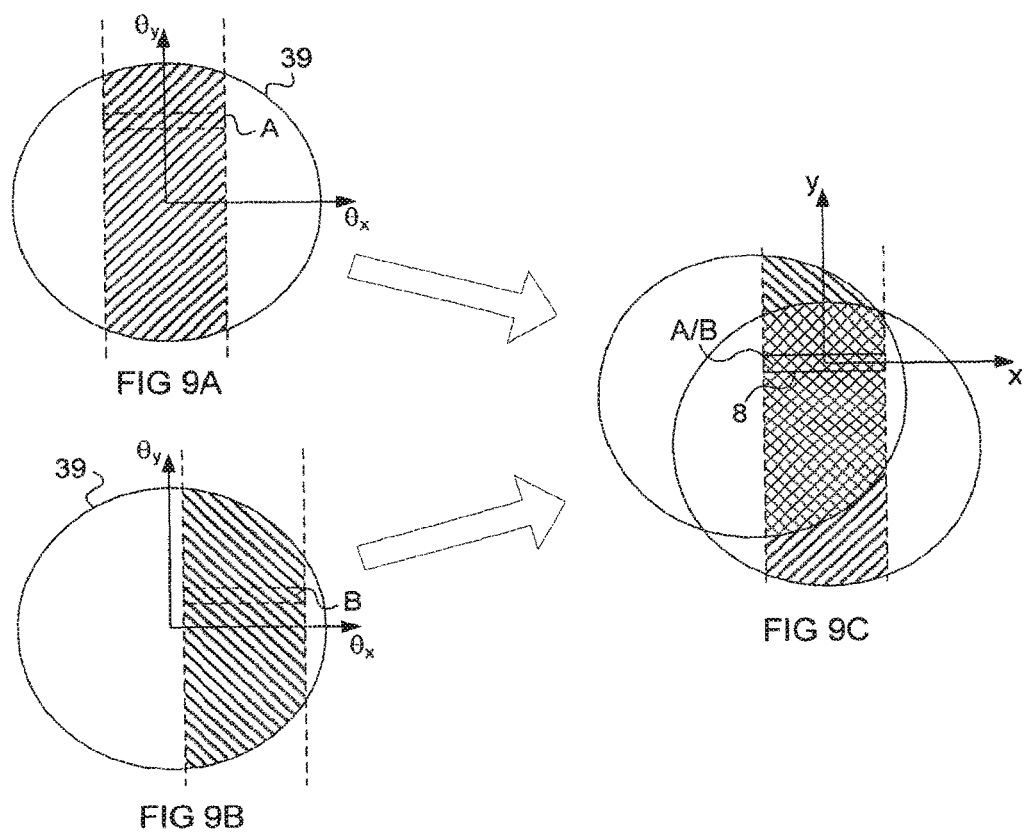

ANALYSER ARRANGEMENT FOR PARTICLE SPECTROMETER

CROSS REFERENCE TO RELATED APPLICATIONS

This application is a continuation of U.S. application Ser. No. 14/363,405, filed Jun. 6, 2014, which is a national phase filing under 35 U.S.C. § 371 of International Application No. PCT/SE2012/050251, filed on Mar. 6, 2012, the contents of which are incorporated herein by reference in its entirety.

TECHNICAL FIELD

The present invention relates to a method and an analyser arrangement for analysing e.g. the energies, the start directions and the start positions of charged particles emitted from a particle emitting sample, and to a particle spectrometer comprising such an analyser arrangement. In particular, the present invention relates to a method and an analyser arrangement for use in a photo-electron spectrometer of hemispherical deflector type.

BACKGROUND

A photo-electron spectrometer of hemispherical deflector type according to prior art is illustrated FIG. 1. In a photo-electron spectrometer 1 of hemispherical deflector type, a central component is the measurement region 3 in which the energies of the electrons are analysed. The measurement region 3 is formed by two concentric hemispheres 5, mounted on a base plate 7, and with an electrostatic field applied between them. The electrons enter the measurement region 3 through an entrance 8 and electrons entering the region between the hemispheres 5 with a direction close to perpendicular to the base plate 7 are deflected by the electrostatic field, and those electrons having a kinetic energy within a certain range defined by the deflecting field will reach a detector arrangement 9 after having travelled through a half circle. In a typical instrument, the electrons are transported from their source (typically a sample 11 that emits electrons after excitation with photons, electrons or other particles) to the entrance 8 of the hemispheres by an electrostatic lens system 13 comprising a plurality of lenses L1-L3 having a common and substantially straight optical axis 15.

For the following description, a Cartesian coordinate system with its z-axis along the optical axis 15 of the lens system 13 (in most cases an axis of rotational symmetry) will be used, and with the hemispheres symmetrical with respect to the (y, z) plane. The directions of the electron trajectories are described by their angles $\theta_x$ against the (y, z) plane and $\theta_y$ against the (x, z) plane.

The lens system 13 and the detector arrangement 9 will only accept electrons which are emitted within a limited area perpendicular to the lens axis 15 and within a limited angular range. Furthermore, the source has to be positioned within a narrow range in the z-direction to achieve the best properties (in terms of sensitivity and resolution). This necessitates mounting the sample on a manipulator 17 allowing both translations and rotations in all coordinate directions, i.e. six degrees of freedom.

In many applications of for example Angle Resolved Photoelectron Spectroscopy (ARPES) a complete measurement requires full detection of a solid angle with a total cone opening of 30 degrees from a well aligned sample. Depending on sample and excitation energy/kinetic energy the required angular range may vary. The angle resolution requirements also varies with application but typically range from 1 degree down to better than 0.1 degrees. In energy resolution the desired span is from 0.5 eV down to 0.5 meV depending on application. In order to achieve a high resolution measurement the analyser arrangement must have sufficient angular and energy resolution, but since the hemispherical analyser arrangement only accepts electrons emitted within a limited angular range perpendicular to the lens axis 15, the sample manipulator 17 must have very high precision movements and repeatability. The manipulator 17 is needed to accurately rotate and tilt the sample to build up the complete 30 degree solid angle data set.

The energy distribution of electrons emitted from a sample is subject to a thermal broadening which is given by $\Delta E = 3.5 * k_B [eV/K] * T[K]$, where $\Delta E$ is the energy distribution in eV, $k_B$ is the Boltzmann constant, and T is the temperature in Kelvin. Therefore, in order to achieve the desired energy resolution it is imperative that the sample 11 can be cooled to very low temperatures, e.g. <1 meV broadening requires a sample temperature of at most 3 K.

The hemispheres 5 disperse the electrons with respect to their energy along the y-direction in the detector plane (which coincide with the plane of entrance 8 of the measurement region 3 in the hemispherical analyser arrangement). In the x-direction, the position in the detector plane is a direct image of the x-coordinate in the plane of the entrance 8 of the hemispheres 5. The entrance 8 of the hemispheres 5 is formed as a narrow slit in the x-direction, hereinafter referred to as the entrance slit of the measurement region or simply the entrance slit. When electrons are allowed into the hemispheres 5 through the narrow entrance slit 8, a two-dimensional detector arrangement 9 will simultaneously give information about the energy distribution and the distribution along the entrance slit 8. The two-dimensional detector arrangement 9 typically comprises a multichannel electron-multiplying plate (MCP) 19 which is arranged in the same plane as the entrance slit 8 of the hemispheres 5 and which generates a measurable electrical signal at the position of an incoming electron, which can then be registered either optically by a phosphorous screen and a video camera 21 or as an electrical pulse e. g. on a delay line or a resistive anode detector. Alternatively, some of the energy-selected electrons may be analysed further, in particular with respect to their spin, after leaving the hemisphere region through an exit aperture 23 leading to a spin detector 25. In one type of spin detector, electrons which leave the hemispheres 5 with a direction close to the (negative) z-direction are transmitted through a sequence consisting of a first lens system, a 90 degree deflector and a second lens system onto a target, after which the distribution of the scattered electrons is measured. Some instruments include two such spin detectors mounted with the deflectors at 90 deg angle to each other (i.e. one bending in the (y, z) and one parallel to the (x, z) plane), with their entrance apertures sitting in the (y, z) symmetry plane of the hemispheres, at different radial (y) positions on each side of an MCP detector.

For a given electrical field between the hemispheres 5, electrons of one particular kinetic energy, called the pass energy ($E_p$), will hit the centre of the MCP detector 19, and a range called the energy window will fall within the sensitive area of the MCP. The energy dispersion (dy/dE) is inversely proportional to $E_p$, while the energy window is directly proportional to $E_p$. In order to achieve a suitable compromise between energy resolution and information rate, it is thus usually necessary to adjust the kinetic energy $E_k$ of the emitted electrons to the proper pass energy. This energy adjustment is performed by the lens system 13. This consists of a series of lens elements L1-L3 in form of concentric electrodes (cylinders, truncated cones, apertures, etc.) arranged along the optical axis 15, each connected to a voltage supply. Besides providing the energy adjustment (acceleration or retardation), the lens system 13 also allows placing the sample at a convenient distance from the hemispheres 5, and, most important in the present context, it can provide control of the distribution of the electrons in the plane of the entrance slit 8 of the hemispheres. The acceleration or retardation is controlled directly by the potential difference between the sample 11 and the hemisphere entrance 8, while the other lens voltages are used to control the electron distribution. The lens system 13 can be operated in two different modes, referred to as imaging and angle-resolving (angular) mode, respectively. In the imaging mode there is (to first order) a point-to-point correspondence between the point of emission and the (x, y) position in the plane of the entrance slit 8, independent of the take-off angle from the sample 11. The entrance slit 8 will then select electrons which are emitted from an area of the sample with the same shape as the entrance slit, and a size given by the lens magnification, i.e. normally within a narrow range in the y-direction. In the angular mode, the lens voltages are instead arranged in such a way that electrons emitted with the same angle $(\theta_x, \theta_y)$ against the lens axis are focused to the same point (x, y) in the plane 26 of the entrance slit 8, as illustrated in FIG. 2, in which the y and z axes are drawn in arbitrary units and to different scales. Here, the final position is to first order independent of the start position, which is then fairly uncritical. The electrons accepted by the entrance slit 8 then have their take-off angles in the y-direction within a narrow range, defined by the entrance slit width and the angular dispersion $(dy/d\theta_y)$, while different take-off angles in the x-direction are distributed along the entrance slit 8. The angular dispersion is however equal in the x and y directions due to the rotational symmetry $(dx/d\theta_x=dy/d\theta_y)$ of the lens system. Both the magnification in the imaging mode and the angular dispersion in the angular mode can be chosen at will and kept constant over large ranges in $(E_k/E_p)$ by adjusting the lens voltages according to pre-calculated functions.

The energy resolution of the hemispheres 5 at a given pass energy is influenced both by the width of the entrance slit 8 and the angular spread of the electron beam in the radial direction as it enters the hemispheres (i.e. spread in dy/dz). For each size of the entrance slit 8 there is a corresponding angular spread which gives the optimum combination of intensity and resolution. For narrow entrance slits, i.e. high energy resolution, the corresponding angular spread is quite small, typically 1-2 deg. This angular spread is defined by combining the entrance slit 8 with another slit 27 (hereinafter referred to as the aperture slit) some distance before it, as illustrated in FIG. 3. In the direction along the entrance slit ((x, z)-plane) there are no such restrictions in angles from resolution requirements. Since the exit angle against the median (y, z) plane after the hemisphere is the same as the entrance angle (dx/dz) against this plane (see in FIG. 1 the trajectory in the median plane and the trajectory in another plane), the directions of those electrons which are intended to reach the spin detector entrance apertures have to be quite close to the z-direction, however.

In order to compensate for misalignment of the emission point of the emitting sample 11 with respect to the optical axis 15 of the lens system 13, one deflector acting in the x-direction and one deflector acting in the y-direction are normally incorporated in the lens system. The x- and y-deflectors may be placed after each other along the lens axis 15, but more often they are combined into one deflector package 29 of four electrodes, each of which covers an azimuthal angle close to 90 deg (see FIG. 1).

Below, some of the problems with particle spectrometers according to prior art will be discussed with reference to FIG. 1. For convenience, the discussion will mainly refer to the angle-resolving (angular) operating mode of the lens system 13. It should be understood, however, that most of the arguments can be equally well applied to mapping in the imaging mode.

The requirement of efficient cooling to very low temperatures implies that the sample 11 has to be in very good thermal contact with the cooling agent, and also efficiently shielded from heat radiation. This is in conflict with the mounting on a manipulator 17 with sufficient degrees of freedom to cover the entire angular range. Mechanical movement of the sample 11 also introduces the risk that the emitting area or the area that is visible to the analyser arrangement of the spectrometer is changed, so spectra taken at different angles are also inadvertently taken from different parts of the sample.

To some extent, it is possible to avoid moving the sample 11 by using the x-deflector and/or the y-deflector described above to guide electrons starting either off-axis (in imaging mode) or with a direction which is not along the optical axis 15 of the lens system 13 (in angular mode) to the centre of the entrance slit 8. A method presented in JP58200144 A2 provides one variation on this theme. The practical applicability of any such approach is quite limited, however, since the trajectories which reach the centre of the entrance slit 8 with this technique will in the general case make an angle against the optical axis 15. For deflection in the y-direction (across the slit) they will then either be stopped by the angle-defining combination of the aperture slit 27 and the entrance slit 8, or give rise to unacceptable loss of energy resolution. In the x-direction (along the slit) only trajectories within a relatively small initial angular range will exit within the angular range accepted by a spin detector system. If the intention is to make use of the entire distribution along the entrance slit 8 there is typically the additional problem that the angular scale is severely distorted even for quite small deflections.

Furthermore, the achievable angular resolution is dependent of the angular dispersion of the lens system 13. This is most clearly seen in the y-direction, where the resolution cannot be better than the entrance slit width divided by the angular dispersion. From this point of view, it is often desirable to be able to work with a large dispersion. On the other hand, the range in θ, that can be observed is limited by the smaller of (length of the hemisphere entrance slit)/(angular dispersion) and the acceptance of the lens front aperture. With increasing dispersion the limitation due to the length of the hemisphere entrance slit may then be too severe, and much smaller than the acceptance of the lens.

SUMMARY OF THE INVENTION

It is an object of the present invention to solve or at least mitigate one or more of the above mentioned problems.

In particular it is an object of the invention to increase the energy resolution in particle spectrometer measurements, such as photo-electron spectrometer measurements.

This and other objects are achieved by a method for determining at least one parameter related to charged particles emitted from a particle emitting sample, e.g. a parameter related to the energies, the start directions, the start positions or the spins of the charged particles. The method comprises the steps of:

forming a particle beam of said charged particles and transporting the particles between said particle emitting sample and an entrance of a measurement region by means of a lens system having a substantially straight optical axis;

deflecting the particle beam in at least a first coordinate direction perpendicular to the optical axis of the lens system before entrance of the particle beam into the measurement region, and detecting the positions of said charged particles in said measurement region, the positions being indicative of said at least one parameter.

Furthermore, the method comprises the step of deflecting the particle beam in the same at least first coordinate direction at least a second time before entrance of the particle beam into the measurement region.

By deflecting the particle beam twice in the same coordinate direction between the particle emitting sample and the entrance of the measurement region, both the position and the direction of the particle beam at the entrance of the measurement region can be controlled.

Preferably, the particle beam is deflected at least twice in each of the two coordinate directions that are perpendicular to the optical axis of the lens system before entrance of the particle beam into the measurement region. This means that given a three dimensional Cartesian coordinate system having its z-axis along the optical axis of the lens system, the particle beam is preferably deflected at least twice in each of the x- and y-directions upstream the entrance of the measurement region from the particles' point of view. In order to fulfil the four conditions (position and direction in two orthogonal directions) at least two degrees of freedom are required in each direction.

The method allows a predetermined part of the angular distribution of the particles forming the particle beam to pass the entrance of the measurement region. Preferably, the deflections of the particle beam are controlled such that said predetermined part of the angular distribution of the particles passes the entrance of the measurement region in a direction being substantially parallel to the optical axis of the lens system. In order to analyse an arbitrary part of the angular distribution of the particle beam (not only a part lying along the x- or y-axis of the above mentioned Cartesian coordinate system), deflection of the particle beam may have to be carried out twice in each of the x- and y-direction before entrance of the particle beam into the measurement chamber.

In one embodiment of the invention, the first and the at least second deflections may be controlled such that said predetermined part of the angular distribution of the particles only includes particles emitted from the sample at a predetermined start direction ($\theta_{x0}$, $h_{y0}$) or within a predetermined range of start directions.

As the method renders possible to make particles emitted in directions that are not parallel to the optical axis of the lens system to enter the entrance of the measurement region in a direction being substantially parallel to the lens axis, the criteria that the sample surface must be oriented with the desired emission angle relative to its normal parallel to the lens axis is eliminated, which in turn reduces the need for moving the test sample to achieve this orientation. Thus, the present invention presents a new type of particle beam manipulation which, to some extent, eliminates the need for physical manipulation of the test sample.

In particular, the proposed particle beam manipulation reduces the need for tilting and rotating the test sample in the x and y-directions of the above mentioned three dimensional Cartesian coordinate system.

Due to the reduced need for complex movability of the manipulator, a manipulator allowing cooling to be applied directly to the test sample can be used. As mentioned above, this provides for more efficient cooling of the test sample which, in turn, results in increased energy resolution in the measurements obtained by the spectrometer analyser. The reduced need for complex movability of the manipulator allows the test sample to be attached directly onto a cooling plate allowing the test sample to be cooled to approximately 2 K, which, with the spectrometer analyser according to the invention, results in an energy resolution of approximately 0.7 meV provided a narrow bandwidth excitation source is used.

Besides the advantage of increased energy resolution with maintained angular resolution, a particle spectrometer comprising an analyser arrangement capable of carrying out the above described method can be manufactured at a lower cost than spectrometers having manipulators offering complex movement of the test sample, such as six-axis manipulators.

Furthermore, the complex movement of the test sample in such a spectrometer according to prior art makes it difficult to continuously irradiate, and hence analyse, a well-defined area of the test sample. As the present invention eliminates the need for complex movement of the test sample, it becomes easier to irradiate and analyse a well-defined target area of the test sample. In particular, the sample position can be kept unchanged during a long series of measurements covering all directions within a solid angle that in many cases is large enough to provide all physically relevant information.

In the measurement region, the charged particles are deflected by an electrostatic field and the positions of the particles after deflection are detected by the detector arrangement. Depending on the design of the measurement region, the entrance of the measurement region and the detector arrangement, various particle-related parameters such as the energies, the start directions or the start positions of the particles can be determined from the detected positions. Preferably, the detection involves detection of the particle positions in two dimensions, one of which substantially represents the energies of the particles and the other which represents a spatial distribution of the particles along a line in the entrance plane of the measurement region. As the spatial distribution of the particles along a line in the entrance plane (typically the longitudinal direction of a slit-shaped entrance) provides information about the start directions or start positions of the particles, the two-dimensional detector arrangement makes it possible to determine both the energies and the start directions or start positions of the particles simultaneously.

Yet another consequence of the ability to control both the position and direction of the particle beam upon entrance into the measurement region is that a larger angular range is accessible for detection as compared to the case with a single deflection of the beam in each coordinate direction. Furthermore the larger angular range can be studied with maintained intensity and resolution (energy and angular). The use of two deflections in the same coordinate direction controlling both position and direction of the particle beam upon entrance into the measurement region makes it possible to study an angular range in solid angle that is substantially defined by the acceptance angle of the lens front aperture without moving the sample. This is not practically possible with a single set of deflectors.

The present invention also provides an analyser arrangement for determining at least one parameter related to charged particles emitted from a particle emitting sample, which analyser arrangement is capable of carrying out the above described method. To this end, the analyser arrangement comprises a measurement region having an entrance allowing the charged particles to enter the measurement region, and a detector arrangement for detecting the positions of the charged particles in the measurement region, which positions are indicative of said at least one parameter. Furthermore, the analyser arrangement comprises a lens system having a substantially straight optical axis, which lens system is operable to form a particle beam of the charged particles emitted from the sample and transporting the particles between the sample and said entrance of the measurement region. The analyser arrangement further includes a deflector arrangement comprising a first deflector for deflecting the particle beam in at least a first coordinate direction perpendicular to the optical axis of the lens system before entrance of the particle beam into the measurement region, and at least a second deflector operable to cause deflection of the particle beam in the same at least first coordinate direction at least a second time before entrance of the particle beam into the measurement region.

Preferably, the at least second deflector is arranged downstream the first deflector at a distance therefrom along the optical axis of the lens system. As understood from the above discussion, the combined effect of the first and the at least second deflector is to control which part of the beam should enter the measurement region and in which direction, which allows a selected part of the beam to enter the measurement region along the direction of the lens axis (i.e. the optical axis of the lens system).

The deflector arrangement is preferably integrated in the lens system of the analyser arrangement, meaning that the lens system and the deflector arrangement form an integral part. This gives a compact design of the analyser and reduces the number of separate parts therein. However, the deflector arrangement may also be arranged upstream or downstream of the lens system of the analyser, in between two lenses of the lens system, or with the at least two deflectors at different positions with respect to the lens system.

For the reasons discussed above, the deflector arrangement is preferably operable to deflect the particle beam twice in each of the coordinate directions that are perpendicular to the optical axis of the lens system, i.e. the x- and y-directions, before the particles of the particle beam passes the entrance of the measurement region.

To this end, the deflector arrangement may comprise e.g. four deflectors, two of which are operable to deflect the particle beam in the x-direction and two of which are operable to deflect the particle beam in the y-direction.

In a preferred embodiment of the invention, the deflector arrangement comprises two deflector packages, each operable to deflect the particle beam in both the x- and the y-direction. To this end, each deflector package may comprise two electrode pairs operable to generate two perpendicular components of an electrical field when a voltage is applied between the electrodes of the respective pairs. The four electrodes of each deflector package are preferably arranged in a formation of essentially quadrupolar symmetry.

The analyser arrangement further comprises a control unit for controlling the deflection of the particle beam by applying controlled voltages to the electrodes of the deflector arrangement.

The control unit may be configured to determine the particular start direction of particles emitted from the sample which enters the measurement region along the optical axis of the lens system by applying deflection voltages according to pre-calculated functions.

In one application, the voltages will be scanned in such a way that a series of start angles $\theta_y$ in the y-direction are successively recorded by the measurement system. For each $\theta_y$, a range of angles $\theta_x$ in the x-direction limited by the slit length of the entrance of the measurement region are recorded, thus providing a two-dimensional map of the angular distribution for each energy within the window defined by the detector system. During such an angular scan, the deflection in the x-direction will typically be kept constant, providing a map over a rectangular area in ($\theta_x$, $\theta_y$). If the lens is operated at high angular dispersion, a number of such scans with different deflections in the x-direction can be combined to give a complete map over the entire angular acceptance of the lens front aperture. To cover energy ranges that are larger than the energy window of the detector, the acceleration/retardation voltage between the sample and the measurement region can also be scanned. This application is applicable but not limited to for example ARPES measurements (Angle Resolved Photoelectron Spectroscopy).

In another application the deflector voltages will be set by the control unit such that particles emitted within a narrow solid angle around one selected direction ($\theta_{x0}$, $\theta_{y0}$) will enter the measurement region along the optical axis of the lens, and after energy analysis particles within a narrow energy range with this particular initial direction are allowed into a spin detector.

In both cases, the control unit will vary the voltages on the lens and deflector electrodes according to pre-calculated functions in order to maintain the focusing and dispersive properties of the lens and to provide the required deflection angles.

In a further embodiment of the invention, voltages of quadrupolar symmetry are superposed on the deflector voltages in at least one deflector package. Such voltages provide focusing in one plane and defocusing in the orthogonal plane, and can be applied in order to reduce distortions in the angular map.

As briefly discussed above, the detector arrangement of the analyser is typically arranged to detect the positions of the charged particles after further deflection of the particles within the measurement region. The magnitude of deflection of a particle depends on the particle's kinetic energy and so the detected position of the particle in a certain direction is indicative of the particle energy. As also mentioned above, the detector arrangement is preferably capable of detecting the two-dimensional positions of the charged particles in the measurement region in order to determine both the energies and the start directions or start positions of the particles. To this end, the detector arrangement may for example comprise a multichannel electron-multiplying plate (MCP) which generates a measurable electrical signal at the position of an incoming particle, which can then be registered either optically by a phosphorous screen and a video camera or as an electrical pulse e. g. on a delay line or a resistive anode detector.

The analyser arrangement is preferably used in a particle spectrometer of the hemispherical deflector type, such as a hemispherical photo-electron spectrometer as described in the background portion. In this case, the measurement region may hence comprise two concentric hemispheres symmetrical with respect to the (y, z) plane of the above mentioned coordinate system. The hemispheres may be mounted on a base plate, and have an electrostatic field applied between them. Particles entering the region between the hemispheres with a direction close to perpendicular to the base plate are deflected by the field, and those electrons having a kinetic energy within a certain range defined by the deflecting field will reach the detector arrangement after having travelled through a half circle. In this embodiment, the entrance of the measurement region, i.e. the entrance into the hemispheres, is typically a slit along the x-direction, which allows a detector arrangement capable of detection in two dimensions to simultaneously give information about the energy distribution and the distribution along the entrance slit, the latter being indicative of either the start directions or start positions of the particles depending on the operational mode of the lens arrangement.

In a refined embodiment of the invention, the analyser arrangement comprises a spin detector. In spin detectors according to prior art, only electrons entering the spin detector within a narrow angular range around the axis of its entrance lens are accepted. In a spectrometer according to prior art, this means that the electrons also have to leave the sample parallel to the direction of the spectrometer lens axis. Yet another advantage of the proposed principle of manipulating the electron beam instead of or in addition to the test sample is that electrons emitted from the sample at any direction within the acceptance of the lens system can be brought to enter the spin detector along the direction of the spin detector entrance lens.

The invention also provides a particle spectrometer, such as a photo-electron spectrometer, comprising an analyser arrangement as described above. In a preferred embodiment, the particle spectrometer is a photo-electron spectrometer of hemispherical deflector type, as described above in the background portion.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

FIGS. 9A to 9C illustrate how selected parts of the angular distribution of emitted particles can be deflected in accordance with the principles of the invention.

DETAILED DESCRIPTION

Figure 1:
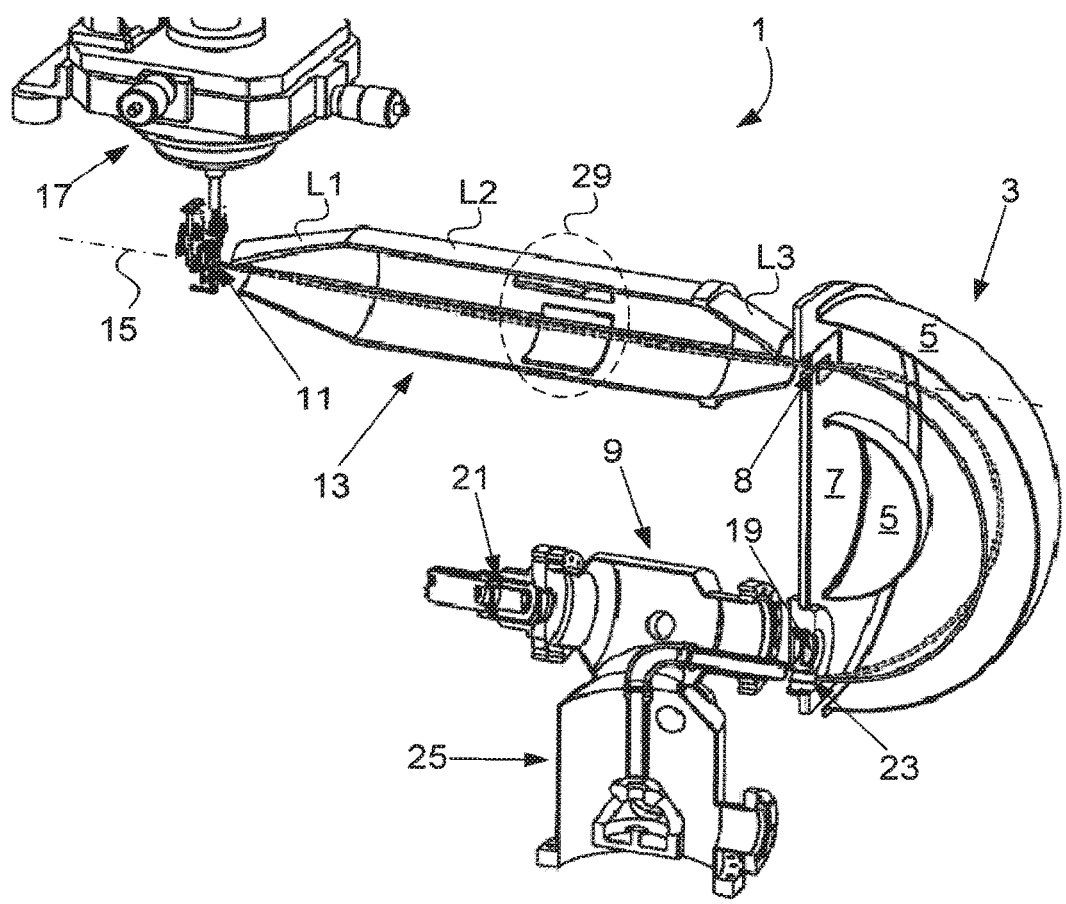
FIG. 1 illustrate a photo-electron spectrometer of hemispherical deflector type according to prior art.
Figure 2:
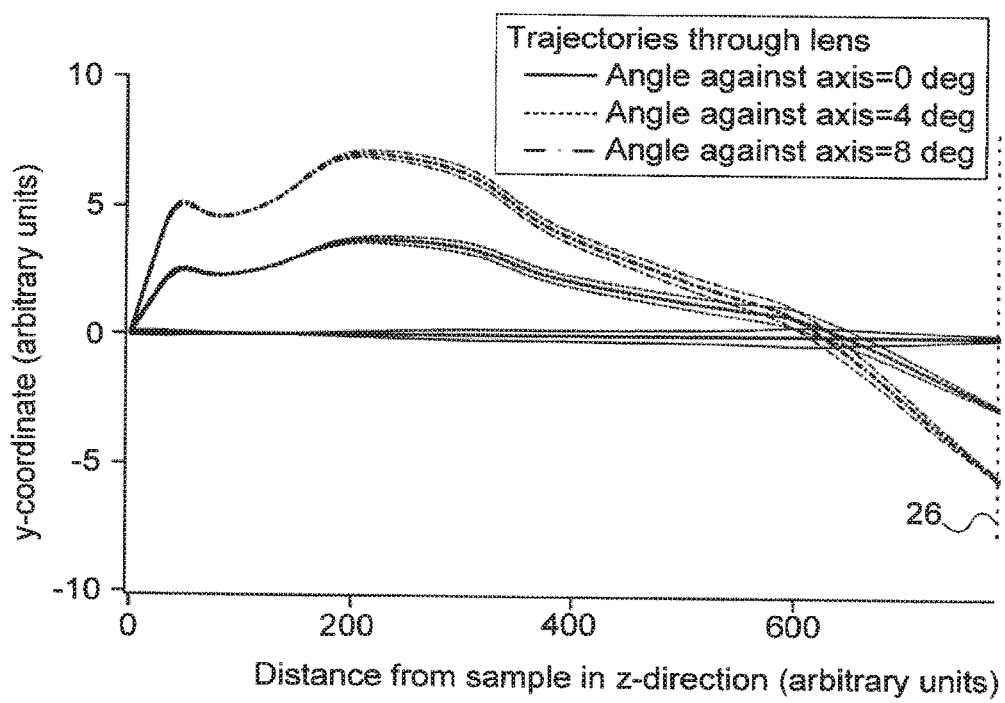
FIG. 2 illustrates particle trajectories through the lens system of the photo-electron spectrometer shown in FIG. 1.
Figure 3:
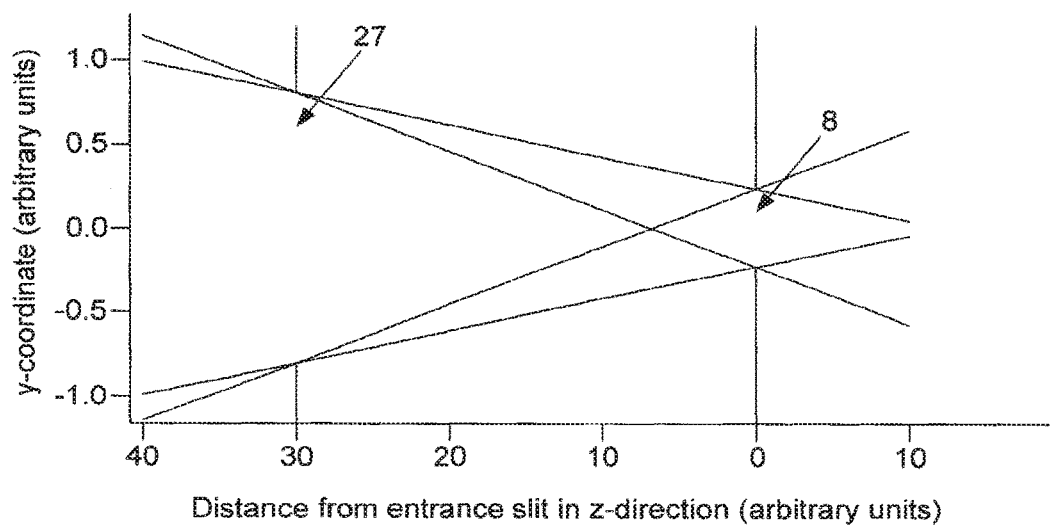
FIG. 3 illustrates an aperture slit and an entrance slit of the measurement region of the photo-electron spectrometer shown in FIG. 1.
Figure 4:
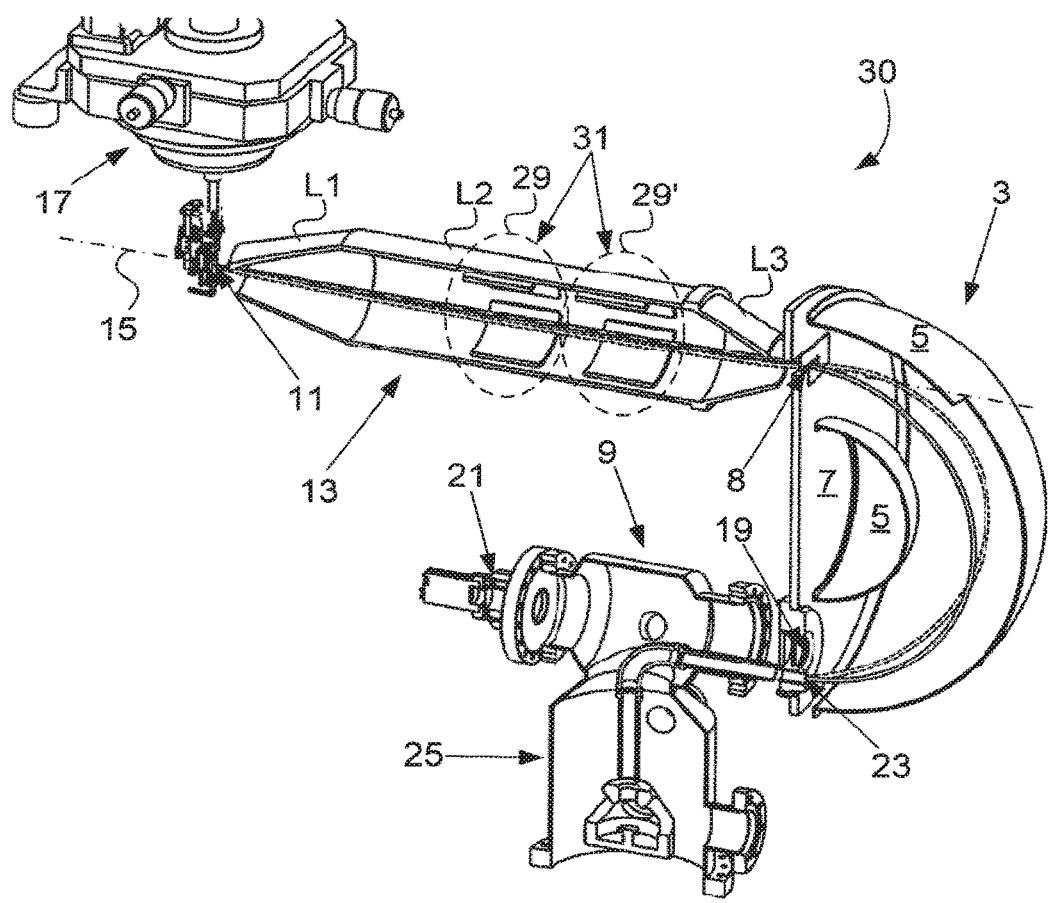
FIG. 4 illustrates a photo-electron spectrometer of hemispherical deflector type according to an exemplary embodiment of the invention.

FIG. 4 illustrates a particle spectrometer 30 according to an exemplary embodiment of the invention. Besides the differences described hereinafter, the components and functionality of the particle spectrometer 30 are identical to the components and functionality of the photo-electron spectrometer 1 of hemispherical deflector type according to prior art, described in the background portion with reference to FIGS. 1 to 3. Elements shown in FIG. 4 that correspond to elements in FIGS. 1 to 3 are provided with the same reference numerals and further descriptions thereof are omitted.

The particle spectrometer 30 is hence a photo-electron spectrometer of hemispherical deflector type comprising an analyser arrangement adapted for analysis of energies and start directions or start positions of charged particles emitted from a particle emitting sample 11.

As seen in FIG. 4, the analyser arrangement includes a deflector arrangement 31 comprising a first deflector package 29 and a second deflector package 29'. Each of the first and the second deflector packages is devised and configured in accordance with the single deflector package 29 of FIG. 1, described in the background portion.

Figure 5A:
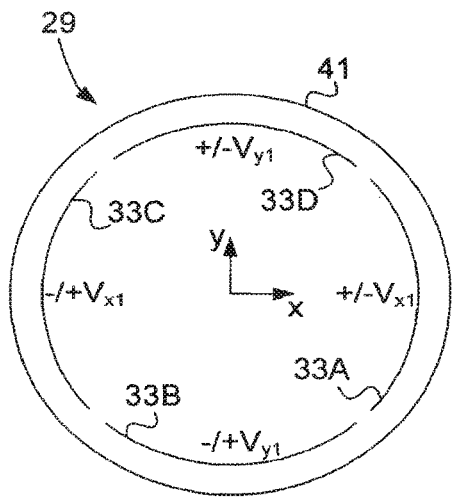
FIGS. 5A and 5B are end views of two deflector packages of an analyser arrangement according to an exemplary embodiment of the invention.
Figure 5B:
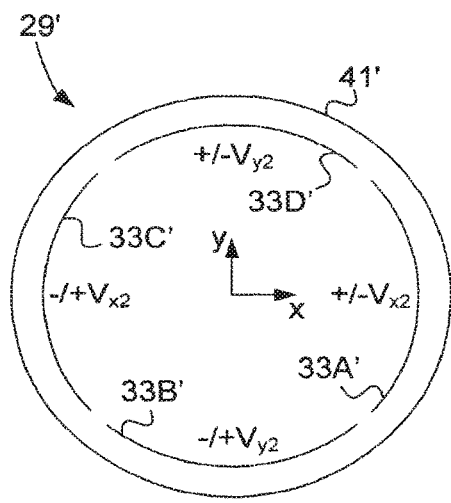

With simultaneous reference to FIGS. 5A and 5B illustrating end views of the first deflector package 29 and the second deflector package 29', respectively, this means that each of the first and the second deflector package comprises four electrodes 33A-33D, 33A'-33D', each of which covers an azimuthal angle close to 90 deg. The two oppositely arranged electrodes in each deflector package form an electrode pair 33A/33C, 33B/33D, 33A'/33C', 33B'/33D' operable to generate an electrical field between them by application of a deflector voltage, $V_x$, $V_y$, and so operable to deflect the charged particles passing between the electrodes of the deflector package in one coordinate direction. Each such electrode pair hence forms a deflector for deflecting the charged particles in one coordinate direction.

Given a three dimensional Cartesian coordinate system with its z-axis along the optical axis 15 of the lens system 13, and with the hemispheres 5 symmetrical with respect to the (y, z) plane, one electrode pair 33A/33C, 33A'/33C' of each deflector package 29, 29' is arranged to deflect the charged particles in the x-direction, and the other electrode pair 33B/33D, 33B'/33D' of each deflector package 29, 29' is arranged to deflect the charged particles in the y-direction. An electrode pair arranged to deflect the charged particles in the x-direction will hereinafter sometimes be referred to as an x-deflector, and an electrode pair arranged to deflect the charged particles in the y-direction will hereinafter sometimes be referred to as the y-deflector.

Figure 6:
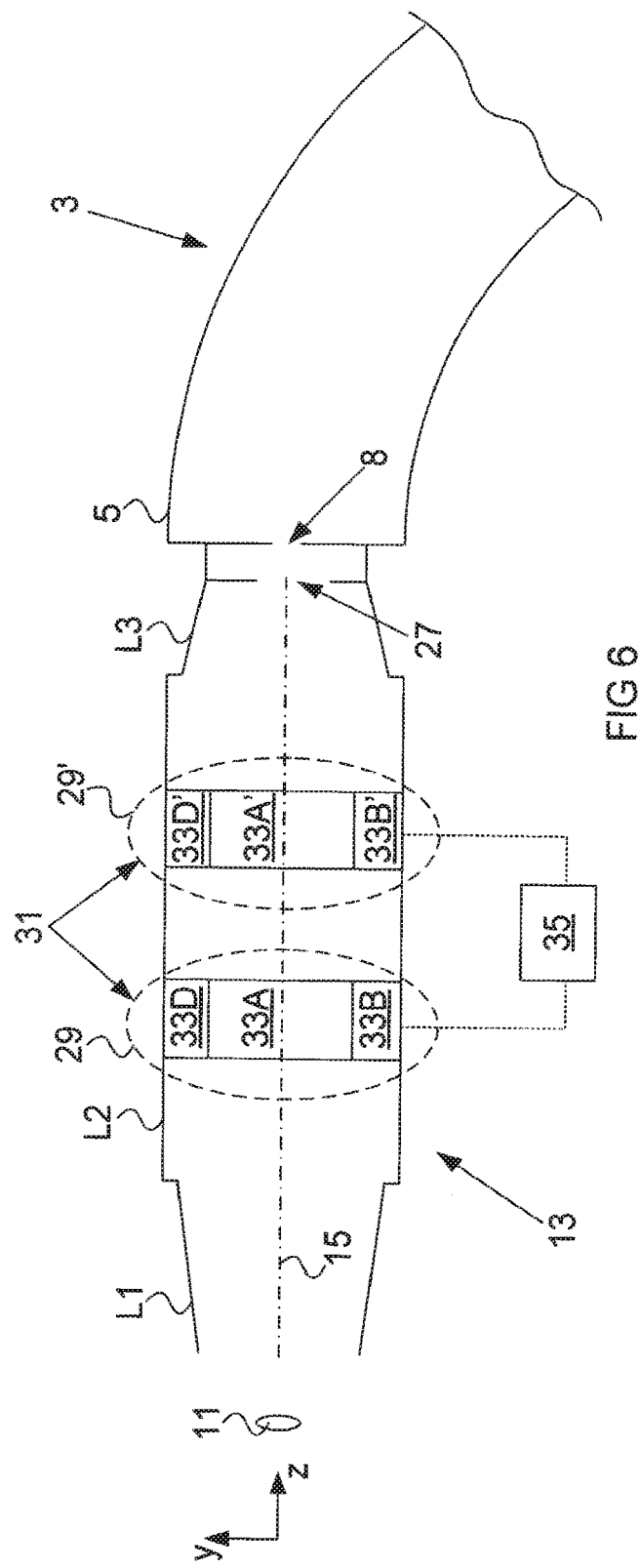
FIG. 6 illustrates parts of an analyser arrangement according to an exemplary embodiment of the invention.

As illustrated in FIG. 6, showing a more detailed view of parts of the analyser arrangement, the deflector voltages applied to the electrodes 33A-33D, 33A'-33D' of the deflector packages 29, 29' are controlled by a control unit 35. The same control unit 35 may also be configured to control the lens voltages applied to a plurality of concentric electrodes constituting the lenses L1-L3 of the lens system 13.

The sign and the magnitude of the deflector voltage, $V_x$, $V_y$, applied between each electrode pair 33A/33C, 33B/33D, 33A'/33C', 33B'/33D' of the deflector arrangement 31 may be independently controlled by the control unit 35. As illustrated in FIGS. 5A and 5B, the deflector voltage of the x-deflector 33A/33C in the first deflector package 29 is denoted $V_{x1}$, and the deflector voltage of the x-deflector 33A'/33C' in the second deflector package 29' is denoted $V_{x2}$. Likewise, the deflector voltages of the y-deflectors 33B/33D, 33B'/33D' in the first and second deflector packages are denoted $V_{y1}$ and $V_{y2}$, respectively.

Thus, the deflector electrodes 33A-33D, 33A'-33D' in each deflector package 29, 29' are so arranged that a voltage, $\Delta V_x$, applied between one pair of opposite electrodes 33A/33C, 33A'/33C' provides deflection only in the x-direction and a voltage, $\Delta V_y$, between the orthogonal pair 33B/33D, 33B'/33D' provides deflection in the y-direction only. Then, any required deflection ($\Delta x'$, $\Delta y'$) can be achieved through the application of a combination of voltages for deflection in the x- and y-directions. By a proper combination of the voltages applied to the deflector electrodes, it is then for any combination of entrance angles of the charged particles into the lens system 13 possible to achieve simultaneously that the exit direction from the deflector region, i.e. the direction of the charged particles when having passed the last deflector of the deflector arrangement 31, is parallel to the lens axis 15, and that the exit occurs along this axis. This means that the trajectory for this particular direction is substantially unchanged by the part of the lens system 13 that is situated after the deflector arrangement 31 (i.e. downstream the deflector arrangement from the particles' point of view).

Figure 7:
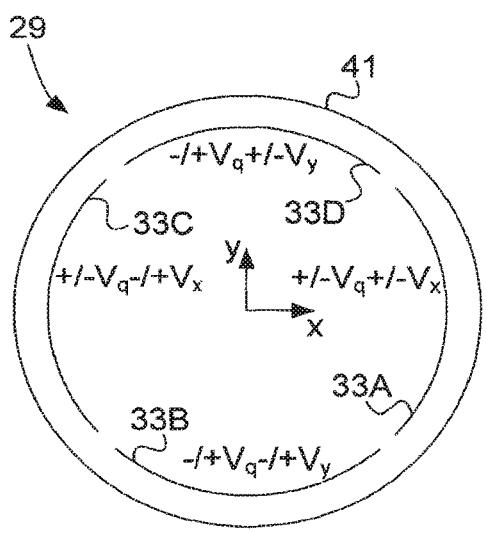
FIG. 7 illustrates an exemplary way in which deflector voltages can be applied to electrodes of the deflector packages shown in FIGS. 5A and 5B.

As illustrated in FIG. 7, voltages $V_q$ of quadrupolar symmetry can be superposed on the deflector voltages $V_x$, $V_y$ applied to the electrodes of the deflector packages. Although FIG. 7 only shows the first deflector package 29 it should be understood that voltages $V_q$ of quadrupolar symmetry can be superposed on the deflector voltages in any or both of the first 29 and second 29' deflector packages. These superposed voltages, $V_q$, are also controlled by the control unit 35 to achieve focusing in one plane and defocusing in the orthogonal plane, thereby reducing distortions in the angular map.

Figure 8A:
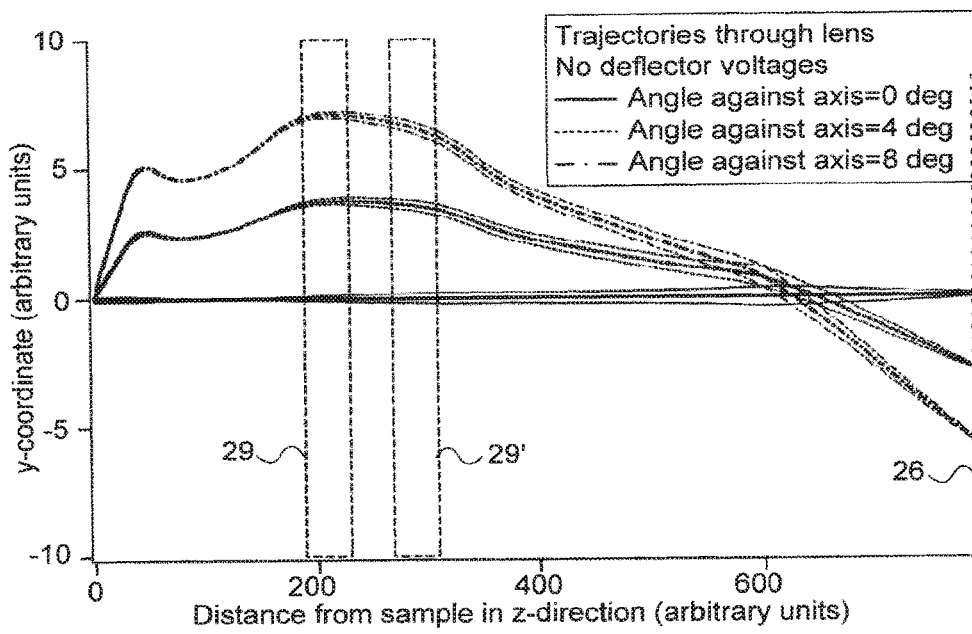
FIGS. 8A and 8B illustrate particle trajectories through the lens system of an analyser arrangement according to the invention, without and with applied deflector potentials.
Figure 8B:
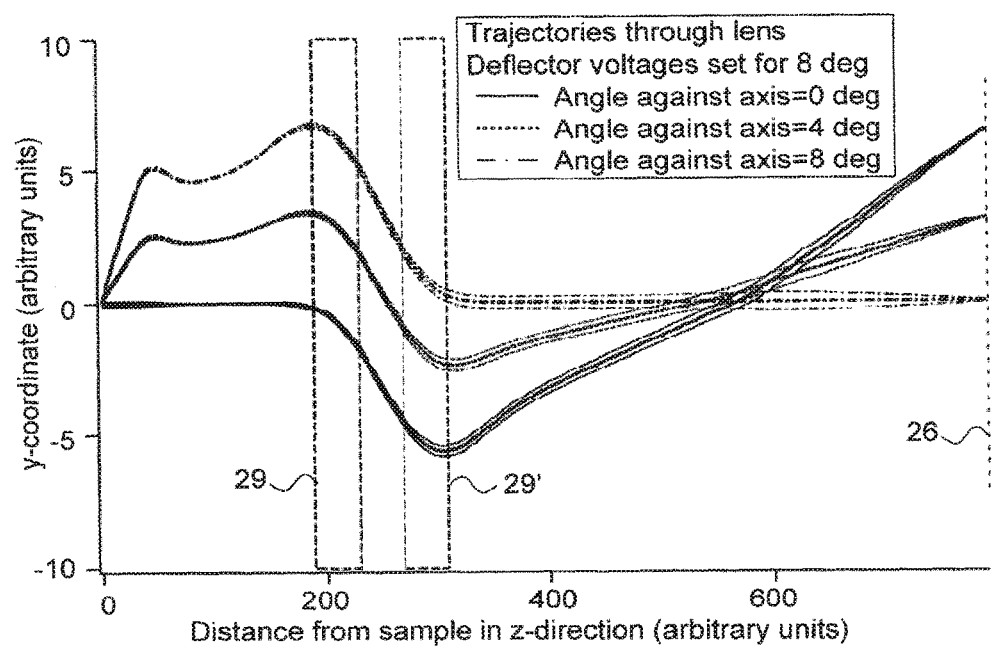

FIGS. 8A and 8B are diagrams showing the projections in the (y,z) plane of some trajectories through the lens system 13 for different start directions of charged particles from the particle emitting sample 11 (located at z=0 and with a small extension around y=0 in the illustrated coordinate systems) without and with deflector potentials $\Delta V_x$, $\Delta V_y$, applied to the first and second deflector packages 29, 29' during angular operational mode of the lens system 13. The vertical axis of the diagrams shows the y-coordinate of the previously discussed three-dimensional coordinate system, and the horizontal axis shows the distance from the sample in the z-direction of the same coordinate system, i.e. the distance from the sample along the optical axis 15 of the lens system 13. The axes are drawn in arbitrary units and to different scales. Trajectories illustrated by continuous lines are trajectories of particles emitted from the sample 11 at a take-off angle of 0 degrees with respect to the optical axis 15 of the lens system while trajectories illustrated by dashed lines and dash-dotted lines illustrate corresponding trajectories for take-off angles of 4 and 8 degrees, respectively.

FIG. 8A illustrates trajectories when the lens system 13 is operated in an angular mode, without deflector voltages applied to the deflector packages 29, 29'. Particles emitted on the lens axis 15 will be guided through the lens system under influence of the different lenses L1-L3 (see FIGS. 4 and 6) to the centre of the plane 26 of the entrance slit 8. Particles emitted with other angles ($\theta_x$, $\theta_y$) to the lens axis will be focused to other defined positions on the entrance slit plane 26.

FIG. 8B illustrates trajectories when the lens system 13 is operated in an angular mode, with deflector voltages $V_x$, $V_y$ applied. In this exemplary embodiment, the deflector voltages applied to the electrodes 33A-33D, 33A'-33D' of the deflector packages 29, 29' are controlled such that a part of the angular distribution of the particles, namely the part comprising particles emitted with a take-off angle of 8 degrees to the lens axis 15, is guided to the centre of the plane of the entrance slit 8, where it enters the measurement region 3 in the direction of the lens axis 15. Particles emitted with other angles ($\theta_x$, $\theta_y$) to the lens axis will be focused to other defined positions on the entrance slit plane.

In this exemplary embodiment, the first deflector package 29 bends the particle trajectories "downwards", while the second deflector package 29' bends in the opposite direction in such a way that the chosen trajectory gently approaches the lens axis 15. Trajectories starting with other directions will leave the lens system at positions which are all displaced by substantially the same amount, keeping the dispersion substantially the same as without deflection.

FIGS. 9A-9C also illustrate how selected parts A, B of the angular distribution of emitted particles can be deflected such that the selected part enters the entrance 8 of the measurement region 3 in a direction being substantially parallel to the optical axis 15 of the lens arrangement using the inventive concept described herein, no matter the take-off angle $\theta_x$, $\theta_y$ from the sample 11. FIGS. 9A and 9B illustrate the angular distribution of the particle beam, denoted by reference numeral 39, and FIG. 9C show these angular distributions mapped onto the hemisphere entrance plane 26 after deflection of the particle beam.

FIGS. 9A and 9C together illustrate a desired deflection of a part A of the angular distribution of the particle beam, and FIGS. 9B and 9C together illustrate a desired deflection of a part B of the angular distribution of the particle beam, which parts A and B comprise particles selected to be analysed in the measurement region 3 with respect to e.g. their energies, start directions, start positions or spin. In accordance with the example illustrated in FIG. 8B, two deflections in a single coordinate direction (the y-direction) is sufficient to make any selected part A of the angular distribution within the strip limited by the dashed vertical lines in FIG. 9A enter the measurement region in a direction being substantially parallel with the lens axis 15, while two deflections in each of the two coordinate directions perpendicular to the lens axis 15 (i.e. the x- and y-directions) are required to make any selected part B of the angular distribution within the strip limited by the dashed vertical lines in FIG. 9B enter the measurement region in a direction being substantially parallel with the lens axis. Any selected part of the angular distribution between the dashed vertical lines in FIG. 9B, with its centre at ($\theta_x$, $\theta_y$), can be made to enter the measurement region if the voltage $V_x$ is set to make trajectories with the fixed start direction $\theta_x \neq 0$ exit with x=0 and dx/dz=0, while the voltage $V_y$ is varied to make successive directions $\theta_y$ exit with y=0 and dy/dz=0.

Once again with reference to FIG. 6, the first 29 and the second 29' deflector packages are arranged concentrically around the optical axis 15 of the lens system 13, separated by some distance, such that the charged particles pass between the electrode pairs 33A/33C, 33B/33D, 33A'/33C', 33B'/33D' of the deflector packages on their way between the particle emitting sample 11 and the entrance 8 of the measurement region 3. For different applications the number of lens elements in the lens arrangement 13 and/or the length of the complete lens arrangement 13 (including the integrated deflector arrangement 31) can vary substantially as different applications may require different combinations of individual lens elements L1, L2, L3. Preferably, none of the deflectors of the deflector arrangement 31 should be located closer to the end of the lens element L2 within which it is arranged than approximately one lens element radius from an end of said lens element L2. Furthermore, the distance between the first 29 and the second 29' deflector packages should preferably be at least the radius of the lens element L2 within which the deflector packages are arranged. Thus, when the first 29 and second 29' deflector packages are arranged within the same lens element L2 having a certain lens element radius, the first deflector package 29 is preferably located at a distance of at least one lens element radius from the front of the lens element L2, and the second deflector package 29' is preferably located at a distance of at least one lens element radius from both the first deflector package 29 and the end of the lens element L2. This is to avoid electrostatic potential cross talk between the first and second deflector package as well as in order to give the charged particle some time to change its direction before entering the next deflector.

Furthermore, the deflectors 33A/33C, 33B/33D, 33A'/33C', 33B'/33D' of the deflector arrangement 31 are preferably so situated with respect to the lens elements L1-L3 of the lens arrangement 13 that the region containing the deflector electrodes and their separation is substantially free from electrical fields other than those generated by the deflector electrodes themselves. To this end, as illustrated in FIGS. 5A and 5B, the deflector electrodes 33A-33D, 33A'-33D' are preferably arranged inside a cylindrical tube 41, 41' with their electrical potentials referred to the potential of this tube. Thus, in the preferred embodiment in which the deflector arrangement 31 comprises two deflector packages 29, 29', each comprising four electrodes 33A-33D, 33A'-33D', the electrodes of each deflector package form cylindrical sectors with a four-fold rotational symmetry so as to form a substantially cylindrically shaped deflector package, which cylindrical deflector package is arranged within an outer cylindrical tube 41, 41'.

Although integrated in the lens system 13 in the exemplary embodiment illustrated in the drawings, it should be appreciated that the deflectors 33A/33C, 33B/33D, 33A'/33C', 33B'/33D' of the deflector arrangement 31 may be arranged in other ways in relation to the lens system 13 and the individual lens elements L1-L3 thereof. For example, the deflector arrangement 31 and all its deflectors might be placed in an "upstream position" between the sample 11 and the front of the lens system 13 or in a "downstream position" between the exit of the lens system 13 and the entrance slit 8 of the hemispheres 5. Such arrangements may be advantageous in some circumstances, insofar that they further decouple the deflection and lens actions. For instance, for a system that is entirely dedicated to observation of one single direction at a time (e. g. a dedicated spin detection system), an upstream position of the deflector arrangement 31 might allow a larger angular range than the integrated solution. The increased distance between the sample 11 and lens arrangement 13 would, however, result in an unfavourable reduction of the angular acceptance for normal applications. With a downstream position of the deflector arrangement 31, the increased distance between the last active lens element L3 and the entrance slit 8 of the measurement region 3 would reduce the flexibility in dispersion and energy range.

Therefore, in a preferred embodiment of the invention, the deflectors 33A/33C, 33B/33D, 33A'/33C', 33B'/33D' of the deflector arrangement 31 are arranged in relation to the individual lens elements L1-L3 of the lens arrangement 13 such that at least one lens acts on the particle beam before the first deflection thereof, and at least one lens acts on the particle beam after the last deflection thereof. Also, all deflectors of the deflector arrangement 31 are preferably arranged within the same lens element L2 of the lens system 13, meaning that all deflectors of the deflector arrangement are surrounded by the same electrical potential. This is advantageous in that it facilitates control of the deflector voltages and lens voltages required to make a desired part of the angular distribution of the particle beam pass the entrance 8 of the measurement region 3 in parallel with the lens axis 15.

As discussed above, in a preferred design, the deflector electrodes are shaped as cylindrical sectors packaged inside two deflector packages 29, 29' with a four-fold rotational symmetry, and the two deflector packages are identical both in cross section and length. However, it should be understood that neither of these features is essential for the operation of the analyser arrangement. Planar or otherwise shaped electrodes are conceivable and might have advantages e. g. to reduce distortions of the angular patterns. Arrangements with 8 (or 4n) poles in at least one of the packages are also possible. Reflection symmetry with respect to the (x, z) and (y, z) planes is highly desirable from the practical point of view, but not strictly necessary.

It should also be understood that the invention is not limited to the embodiments described above, but can be varied within the scope of the subsequent claims.

The invention claimed is:

1. A method for determining energies and start directions related to charged particles emitted from a particle emitting sample, comprising the steps of:
   forming a particle beam of said charged particles and transporting the particles between said particle emitting sample and an entrance of a measurement region by a lens system having a substantially straight optical axis;
   deflecting the particle beam in at least a first coordinate direction perpendicular to the optical axis of the lens system before entrance of the particle beam into the measurement region;
   deflecting the particle beam in said at least first coordinate direction at least a second time before entrance of the particle beam into the measurement region;
   detecting the positions of said charged particles in said measurement region, the positions being indicative of said energies and start directions; and
   controlling the deflections of the particle beam such that a predetermined part of the angular distribution of the particles forming the particle beam passes the entrance of the measurement region.

2. The method according to claim 1, wherein the first deflection of the particle beam is effectuated by means of a first deflector, and the at least second deflection of the particle beam is effectuated by means of at least a second deflector arranged downstream of the first deflector at a distance therefrom along the optical axis of the lens system.

3. The method according to claim 1, wherein the particle beam is deflected at least twice also in a second coordinate direction perpendicular to the first coordinate direction and the optical axis of the lens system before entrance of the particle beam into the measurement region.

4. The method according to claim 1, wherein all deflections of the particle beam takes place within the lens system, meaning that at least one lens acts on the particles before the first deflection of the particle beam and at least one lens acts on the particles after the last deflection of the particle beam.

5. The method according to claim 1, wherein at least one deflection of the particle beam is effectuated by means of a deflector package comprising four electrodes arranged in a formation of essentially quadrupolar symmetry wherein the four electrodes form two electrode pairs serving as deflectors in a respective coordinate direction, further comprising the steps of:
applying a first deflector voltage between one of the two electrode pairs of the deflector package;
applying a second deflector voltage between the other electrode pair of the deflector package, and
applying voltages of quadrupolar symmetry to the electrodes of the deflector package, superposed on said deflection voltages.

6. The method according to claim 1, further comprising the step of controlling the deflections of the particle beam such that said predetermined part of the angular distribution of the particles passes the entrance of the measurement region in a direction being substantially parallel to the optical axis of the lens system.

7. The method according to claim 1, wherein the step of detecting the positions of the charged particles involves detection of the positions in two dimensions, one of which is indicative of the energies of the particles and one of which is indicative of the start directions or the start positions of the particles.

8. An analyser arrangement for determining energies and start directions related to charged particles emitted from a particle emitting sample, comprising:
a measurement region having an entrance allowing said particles to enter the measurement region;
a lens system for forming a particle beam of said charged particles and transporting the particles between said particle emitting sample and said entrance of the measurement region, said lens system having a substantially straight optical axis;
a deflector arrangement comprising a first deflector for deflecting the particle beam in at least a first coordinate direction perpendicular to the optical axis of the lens system before entrance of the particle beam into the measurement region and a second deflector for deflecting the particle beam in said at least first coordinate direction at least a second time before entrance of the particle beam into the measurement region;
a detector arrangement for detecting the positions of the charged particles in the measurement region, said positions being indicative of said energies and start directions; and
a control unit operable to cause the deflector arrangement to deflect the particle beam such that a predetermined part of the angular distribution of the particles forming the particle beam passes the entrance of the measurement region.

9. The analyser arrangement according to claim 8, wherein the second deflector is arranged downstream the first deflector at a distance therefrom along the optical axis of the lens system.

10. The analyser arrangement according to claim 8, wherein the deflector arrangement is operable to cause deflection of the particle beam at least twice also in a second coordinate direction perpendicular to the first coordinate direction and the optical axis of the lens system before entrance of the particle beam into the measurement region.

11. The analyser arrangement according to claim 10, wherein the deflector arrangement comprises at least one deflector package comprising four electrodes arranged in a formation of essentially quadrupolar symmetry wherein the four electrodes of the deflector package form two electrode pairs serving as deflectors in a respective coordinate direction of said first and second coordinate directions.

12. The analyser arrangement according to claim 11, further comprising a control unit configured to apply individual voltages to each of the electrodes.

13. The analyser arrangement according to any of the claim 12, wherein the deflector arrangement and the lens system are arranged such that at least one lens element of the lens system is positioned upstream of all deflectors of the deflector arrangement and at least one other lens element of the lens system is positioned downstream of all deflectors of the deflector arrangement.

14. The analyser arrangement according to any of the claim 13, wherein all deflectors of the deflector arrangement are arranged within the same lens element of the lens arrangement.

15. The analyser arrangement according to any of the claims 14, wherein the deflector arrangement form an integral part of the lens system.

16. The analyser arrangement according to claim 8, wherein the control unit is operable to cause the deflector arrangement to deflect the particle beam such that said predetermined part of the angular distribution of the particles passes the entrance of the measurement region in a direction being substantially parallel to the optical axis of the lens system.

17. The analyser arrangement according to any of the claim 16, wherein the detector arrangement is configured to determine the positions of the charged particles in two dimensions, one of which is indicative of the energies of the particles and one of which is indicative of the start directions or the start positions of the particles.

18. A particle spectrometer for analysing a particle emitting sample, wherein the particle spectrometer comprises an analyser arrangement according to claims 8.

19. A particle spectrometer according to claim 18, wherein said particle spectrometer is a photo-electron spectrometer of hemispherical deflector type.

* * * * *